(12) United States Patent  
Cryer et al.

(10) Patent No.: US 6,290,710 B1  
(45) Date of Patent: Sep. 18, 2001

(54) EMBOLIC PROTECTION DEVICE

(75) Inventors: Brett W. Cryer, Stanford; Michael S. Mirizzi, San Jose, both of CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/474,557

(22) Filed: Dec. 29, 1999

(51) Int. Cl.[7] ............................................... A61M 29/00
(52) U.S. Cl. ........................ 606/200; 606/198; 606/195; 606/191; 606/159
(58) Field of Search .................................. 606/200, 198, 606/195, 191, 159

(56) References Cited

U.S. PATENT DOCUMENTS 3,952,747 * 4/1976 Kimmell, Jr. .  
4,425,908 * 1/1984 Simon .

(List continued on next page.)

FOREIGN PATENT DOCUMENTS

| 0 427 429 A2 | 5/1991 | (EP) . |
| 0 472 334 A1 | 2/1992 | (EP) . |
| WO92/03097 | 3/1992 | (WO) . |
| WO96/01591 | 1/1996 | (WO) . |
| WO97/17100 | 5/1997 | (WO) . |
| WO99/23976 | 5/1999 | (WO) . |

*Primary Examiner*—Gary Jackson  
(74) *Attorney, Agent, or Firm*—Fulwider Patton Lee & Utecht, LLP (57) ABSTRACT

A self-expanding filtration element is fitted to the distal end of a catheter while a sheath for constraining such element to a reduced diameter is mechanically manipulatable from the proximal end of the device. The entire device is maneuvered into position over a guide wire and deployed prior to treatment of the body lumen at an upstream location. After completion of the treatment procedure, the filtration element is collapsed and constrained within the sheath to retain any embolic material that has been captured and allow it to be safely removed from the vasculature. The device may be combined with a primary treatment modality and its low profile allows the constrained filtration element to be removed through a deployed stent.

16 Claims, 6 Drawing Sheets

U.S. PATENT DOCUMENTS

| | | | |
|---|---|---|---|
| 4,494,531 | * | 1/1985 | Gianturco . |
| 4,612,931 | * | 9/1986 | Dormia . |
| 4,619,246 | * | 10/1986 | Molgaard-Nielsen et al. . |
| 4,643,184 | * | 2/1987 | Mobin-Uddin . |
| 4,650,466 | * | 3/1987 | Luther . |
| 4,662,885 | * | 5/1987 | DiPisa, Jr. . |
| 4,688,553 | * | 8/1987 | Metals . |
| 4,706,671 | * | 11/1987 | Weinrib . |
| 4,723,549 | * | 2/1988 | Wholey et al. . |
| 4,727,873 | * | 3/1988 | Mobin-Uddin . |
| 4,781,177 | * | 11/1988 | Lebigot . |
| 4,790,812 | * | 12/1988 | Hawkins, Jr. et al. . |
| 4,790,813 | | 12/1988 | Kensey . |
| 4,794,928 | | 1/1989 | Kletschka . |
| 4,832,055 | | 5/1989 | Palestrant . |
| 4,873,978 | | 10/1989 | Ginsburg . |
| 4,921,478 | | 5/1990 | Solano et al. . |
| 4,921,484 | | 5/1990 | Hillstead . |
| 4,969,891 | | 11/1990 | Gewertz . |
| 4,990,156 | | 2/1991 | Lefebvre . |
| 4,997,435 | | 3/1991 | Demeter . |
| 4,998,539 | | 3/1991 | Delsanti . |
| 5,053,008 | | 10/1991 | Bajaj . |
| 5,064,428 | | 11/1991 | Cope et al. . |
| 5,071,407 | | 12/1991 | Termin et al. . |
| 5,092,839 | | 3/1992 | Kipperman . |
| 5,100,425 | | 3/1992 | Fischell et al. . |
| 5,102,415 | | 4/1992 | Guenther et al. . |
| 5,108,419 | | 4/1992 | Reger et al. . |
| 5,152,777 | | 10/1992 | Goldberg et al. . |
| 5,160,342 | | 11/1992 | Reger et al. . |
| 5,192,286 | | 3/1993 | Phan et al. . |
| 5,324,304 | | 6/1994 | Rasmussen . |
| 5,329,942 | | 7/1994 | Gunther et al. . |
| 5,330,482 | | 7/1994 | Gibbs et al. . |
| 5,350,398 | | 9/1994 | Pavcnik et al. . |
| 5,370,657 | | 12/1994 | Irie . |
| 5,383,887 | | 1/1995 | Nadal . |
| 5,421,832 | | 6/1995 | Lefebvre . |
| 5,490,859 | | 2/1996 | Mische et al. . |
| 5,496,277 | | 3/1996 | Termin et al. . |
| 5,496,330 | | 3/1996 | Bates et al. . |
| 5,501,694 | | 3/1996 | Ressemann et al. . |
| 5,549,626 | | 8/1996 | Miller et al. . |
| 5,601,595 | | 2/1997 | Smith . |
| 5,626,605 | | 5/1997 | Irie et al. . |
| 5,634,942 | | 6/1997 | Chevillon et al. . |
| 5,649,953 | | 7/1997 | Lefebvre . |
| 5,662,671 | | 9/1997 | Barbut et al. . |
| 5,669,933 | | 9/1997 | Simon et al. . |
| 5,681,347 | | 10/1997 | Cathcart et al. . |
| 5,695,518 | | 12/1997 | Laerum . |
| 5,695,519 | | 12/1997 | Summers et al. . |
| 5,720,764 | | 2/1998 | Naderlinger . |
| 5,725,550 | | 3/1998 | Nadal . |
| 5,746,767 | | 5/1998 | Smith . |
| 5,755,790 | | 5/1998 | Chevillon et al. . |
| 5,769,816 | | 6/1998 | Barbut et al. . |
| 5,772,674 | | 6/1998 | Nakhjavan . |
| 5,779,716 | | 7/1998 | Cano et al. . |
| 5,792,145 | | 8/1998 | Bates et al. . |
| 5,792,156 | | 8/1998 | Perouse . |
| 5,792,157 | | 8/1998 | Mische et al. . |
| 5,795,322 | | 8/1998 | Boudewijn . |
| 5,800,457 | | 9/1998 | Gelbfish . |
| 5,800,525 | | 9/1998 | Bachinski et al. . |
| 5,810,874 | | 9/1998 | Lefebvre . |
| 5,814,064 | | 9/1998 | Daniel et al. . |
| 5,827,324 | | 10/1998 | Cassell et al. . |
| 5,833,650 | | 11/1998 | Imran . |
| 5,836,868 | | 11/1998 | Ressemann et al. . |
| 5,846,251 | | 12/1998 | Hart . |
| 5,846,260 | | 12/1998 | Maahs . |
| 5,848,964 | | 12/1998 | Samuels . |
| 5,868,708 | | 2/1999 | Hart et al. . |
| 5,876,367 | | 3/1999 | Kaganov et al. . |
| 5,897,567 | | 4/1999 | Ressemann et al. . |
| 5,910,154 | | 6/1999 | Tsugita et al. . |
| 5,911,734 | | 6/1999 | Tsugita et al. . |
| 5,941,896 | | 8/1999 | Kerr . |
| 5,968,071 | | 10/1999 | Chevillon et al. . |
| 5,976,172 | | 11/1999 | Homsma et al. . |
| 5,980,555 | | 11/1999 | Barbut et al. . |
| 5,989,281 | | 11/1999 | Barbut et al. . |
| 6,001,118 | | 12/1999 | Daniel et al. . |
| 6,013,093 | | 1/2000 | Nott et al. . |

\* cited by examiner

EMBOLIC PROTECTION DEVICE

BACKGROUND OF THE INVENTION

The present invention generally relates to embolic protection systems and more particularly pertains to emboli capturing devices for use in conjunction with devices for intravascularly treating stenosed blood vessels. The system allows a vascular site to be treated while embolic materials that are intentionally or accidentally dislodged by such treatment are collected and retrieved.

Blood vessels can become stenosed or completely occluded in a number of different ways. A stenosis may for example be formed by an atheroma which is typically a fatty, fibrous or hard and calcified substance that forms on the lumen walls of the blood vessel. Alternatively, the stenosis may be formed of thrombus material which is typically much softer than an artheroma but can nonetheless cause restricted blood flow in the lumen of the blood vessel. Thrombus formation can be particularly problematic in a saphenous vein graft as well as in carotid artery and intracranial vessel disease due to the potential for thromboembolic stroke.

A variety of intravascular procedures have been developed for restoring the patency of certain stenosed or occluded blood vessels. The device or devices that are employed for such treatment are introduced into the vasculature at a readily accessible location and advanced therethrough to the stenosed site. In balloon angioplasty, a balloon-tipped catheter is positioned within the stenosed region of the blood vessel where it is inflated to dilate the lumen. A stent may additionally be deployed in the dilated region in order to continue to support the walls of the blood vessel after the balloon has been deflated and removed. Alternatively, the obstructing plaque or thrombosis may be mechanically removed or ablated in an effort to restore patency.

One problem common to all of these techniques is the potential for the escape of portions of the plaque or thrombus, resulting in emboli being carried downstream to lodge elsewhere in the vascular system. Such emboli can be extremely dangerous to the patient, capable of causing severe impairment of the circulatory system. Depending on where the embolic material is released, a heart attack or stroke could result, or in the event peripheral circulation is severely compromised, the amputation of a limb may become necessary.

Previously suggested approaches for dealing with embolic debris or fragments have included cutting the debris into very small pieces of a size on the order of blood cells so as to preclude the formation of occlusions at downstream locations. Such technique does however have certain problems including for example the difficulty inherent in trying to control the size of the fragments that are severed. Additionally, since a thrombus is much softer than an atheroma, it tends to break up more easily when mechanically engaged by a cutting instrument, thus creating the risk of causing large fragments to become dislodged when the thrombus is mechanically engaged.

Suction techniques have also been employed in an effort to remove debris immediately after it has been severed or otherwise dislodged from the lumen walls. It is however necessary to pull quite a high vacuum in order to ensure removal of all of the pieces severed from a stenosis. When an excessively high vacuum is employed, the vasculature may be subject to collapse. On the other hand, if an insufficiently high vacuum is drawn, all of the debris that has been severed may not be removed.

As a further alternative for preventing dislodged plaque from posing an embolic risk, various embolic capturing devices have to date been developed. Such devices are deployed downstream of the stenotic site being treated and serve to filter or strain the blood of any embolic material that exceeds a certain minimum size. Upon completion of the treatment procedure, the capturing device is retracted to remove the captured embolic material from within the vasculature.

A difficulty inherent in the use of such devices is the limited amount of space that is available within the vasculature. The device must be dimensioned and configured to permit it to be introduced into the vasculature, maneuvered therethrough and positioned downstream of the treatment site. This may involve passage through significant convolutions at some distance from the initial point of introduction. Once in position, the device must be deployable to a sufficiently large cross-section to effectively strain substantially all of the blood passing therethrough without unacceptably reducing its flowrate. Additionally, the use or the presence of such device must not interfere with the treatment of the vasculature site, nor may the treating device interfere with the function of the embolic capture device.

Some of the heretofore known devices employ a guide wire based configuration wherein the embolic capture device is affixed to the distal end of a guide wire or guide wire-like element. Such approach either requires the guide wire element to actually function as the primary access guide wire or requires the capture device, including its deployment mechanism, to be dimensioned so as to be extendable through a catheter lumen. While the former approach enables the emboli capture device to be dimensioned much larger than what would be able to pass through a catheter lumen, the association of the capture device with the guide wire severely compromises the ultimate flexibility and maneuverability of the guide wire and thereby limits its ability to access hard to reach destinations. On the other hand, while the latter approach allows a primary access guide wire to be used to gain initial access whereby full advantage can be taken of such wire's flexibility and low profile, the initial access wire must subsequently be swapped for the embolic capture carrying wire. Such task can be rather time consuming and problematic. Moreover, because the embolic capture device carrying wire must be extended through the catheter lumen, its maximum cross section is severely limited. Its effectiveness to strain the blood is thereby limited as is its ability to retrieve the collected embolic material.

It would be most desirable for an embolic protection device to be sufficiently sized to be able to effectively strain the blood flowing therethrough without limiting blood flow and without requiring a change out with a guide wire. More particularly, it would be desirable for the emboli capturing device to be of an over-the-wire design of a configuration that would not to interfere with the treatment of the vessel upstream therefrom and wherein such treatment does not interfere with the function of the emboli capturing device.

SUMMARY OF THE INVENTION

The embolic protection device of the present invention overcomes the shortcomings of the previously known devices. The device has an over-the-wire configuration which obviates the need to change out guide wires during the procedure. Additionally, the configuration of the device allows it to be initially deployed downstream of the treatment site and after the treatment is complete, allows the device along with any captured embolic debris to be removed without interfering with treatment procedure or treated site.

The device of the present invention is able to achieve such objectives by providing a self-expanding filtration element that is affixed to the distal end of a catheter having at least one lumen formed therein. The filtration member is formed of super-elastic material such as Nitinol or a polymer that assumes a generally conical shape when not constrained. Such filtration element is oriented such that its expanded diameter projects either proximally or distally relative to its point of attachment on the catheter.

A sheath element is configured and dimensioned to restrain the filtration element to a sufficiently low profile to facilitate its advancement and retraction through the vasculature including, optionally, its passing through a stent that has been deployed in the vasculature. The sheath is manipulated relative to the filtration device either by an inner member of tubular configuration that is concentrically disposed with the catheter lumen and about the guide wire or by a push wire that extends through a second lumen formed in the catheter. Alternatively, an outer member concentrically disposed about the catheter may be employed to manipulate the position of the sheath at the distal end of the catheter. In either configuration, both the catheter as well as the element attached to the sheath extend to the proximal end of the device to enable the relative position of the filtration element and sheath to be shifted from outside of the vasculature.

The various embodiments of the present invention provide for either the subsequent advancement of a primary treatment modality over the catheter of the embolic protection device or for a primary treatment modality to be affixed directly to the catheter. In the latter embodiment, the outer member serves both as the sheath to constrain the filtration element as well as to protect the balloon or stent during advancement through the vasculature. Alternatively, the outer member may additionally serve to constrain a self-expanding stent prior to deployment.

These and other features and advantages of the present invention will become apparent from the following detailed description of preferred embodiments which, taken in conjunction with the accompanying drawings, illustrate by way of example the principles of the invention.

DETAILED DESCRIPTION OF THE PREFERRED EMBODIMENTS

The figures generally illustrate the present invention. The device is deployed prior to intravasculature procedures that run the risk of dislodging embolic material. Any such material that becomes dislodged is captured by the device and removed after the procedure is completed. Alternatively, the device may be deployed to retrieve or otherwise neutralize a clot.

Figure 1:
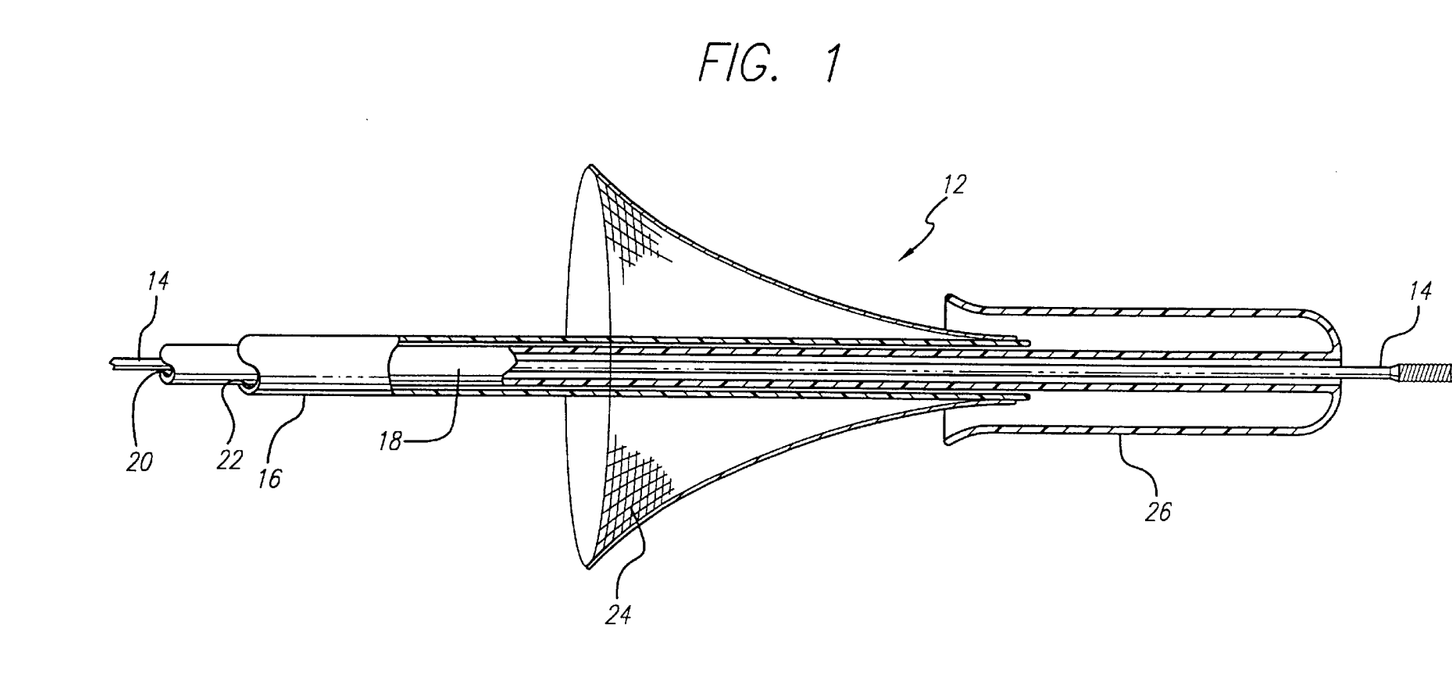
FIG. 1 is an enlarged, partial cross-sectional view of an embolic protection device of the present invention.

The embodiment illustrated in FIG. 1 shows an embolic protection device 12 of the present invention fitted about a guide wire 14. A catheter shaft 16 and inner member 18 are concentrically fitted about such guide wire. The inner member has a lumen 20 formed therein, sized to accommodate the guide wire. The catheter has a lumen 22 formed therein, sized to receive the inner member. Both the catheter and inner member extend proximally a sufficient distance so as to be manipulatable from outside of the patient's vasculature. A generally conically shaped filtration element 24 is affixed to the distal end of the catheter. The filtration element is formed from a shape memory material that causes the proximal end of the filtration element to expand when unrestrained to a diameter that has been selected for straining the blood flowing through the particular body lumen in which it is to be deployed. This may either entail substantially conforming to the inner diameter of such body lumen or alternatively, may be selected to be less than the diameter of such lumen to enable the device to "float" within in the lumen to avoid making contact with the lumen walls in an effort to avoid further plaque disruptment. The filtration element includes a webbing structure wherein the size of the void spaces is selected to capture material larger than a minimum size which has been deemed acceptable for a particular application. The inner member has sheath 26 fitted to its distal end. The dimensions of such sheath are selected to receive and constrain the filtration element to a reduced diameter. Longitudinally shifting the inner member relative to the catheter causes the sheath to uncover and re-cover the filtration element. The filtration element's elasticity causes the element to expand when outside of the sheath. Forcing the filtration element into the sheath, or alternatively, pulling the sheath over the element causes the filtration element to become reduced in size. The entire filtration element may be formed of Nitinol or of a polymeric material. Alternatively, a hybrid construction may be used wherein portions of the filtration element may be formed of for example Nitinol and other portions are formed of a polymeric material. Both the catheter and the inner member are preferably coated with a lubricious substance in order to reduce friction during the relative movement of the two elements as well as the movement of a primary treatment modality over the exterior surface of the catheter.

In use, the guidewire 14 is first maneuvered into position through the vasculature and through the treatment site to a position downstream thereof. With the filtration element 24 fully constrained within the sheath 26, the catheter shaft 16 and inner member 18 combination are advanced along the guide wire to a point beyond and downstream of the treatment site. The filtration element is then deployed either by holding the inner member in position and retracting the catheter slightly, or by holding the catheter in position and advancing the inner member slightly to free the filtration element from the sheath. The super-elastic material employed in the manufacture of the filtration element causes such element to assume its expanded shape immediately upon release from under the sheath. After deployment, a primary treatment modality is advanced into position over the catheter. Such modality could include a balloon catheter or a stent delivery device. After completion of the procedure, the primary treatment modality is removed from the vasculature after which the filtration element is either pulled into the sheath or the sheath is pulled over the filtration element. Any embolic material that had been captured is thereby tightly constrained within the filtration element and sheath, and the entire combination can then be safely removed from the patient's vasculature. Alternatively, the device may be utilized as a stand-alone clot puller without use of a primary treatment modality. Such device could be used in the treatment of acute thromboembolic stroke wherein the device is advanced to just beyond the clot and deployed to capture the embolic material. The clot is then removed with the removal of the device or relocated to peripheral vasculature more capable of tolerating the presence of such material.

Figure 2:
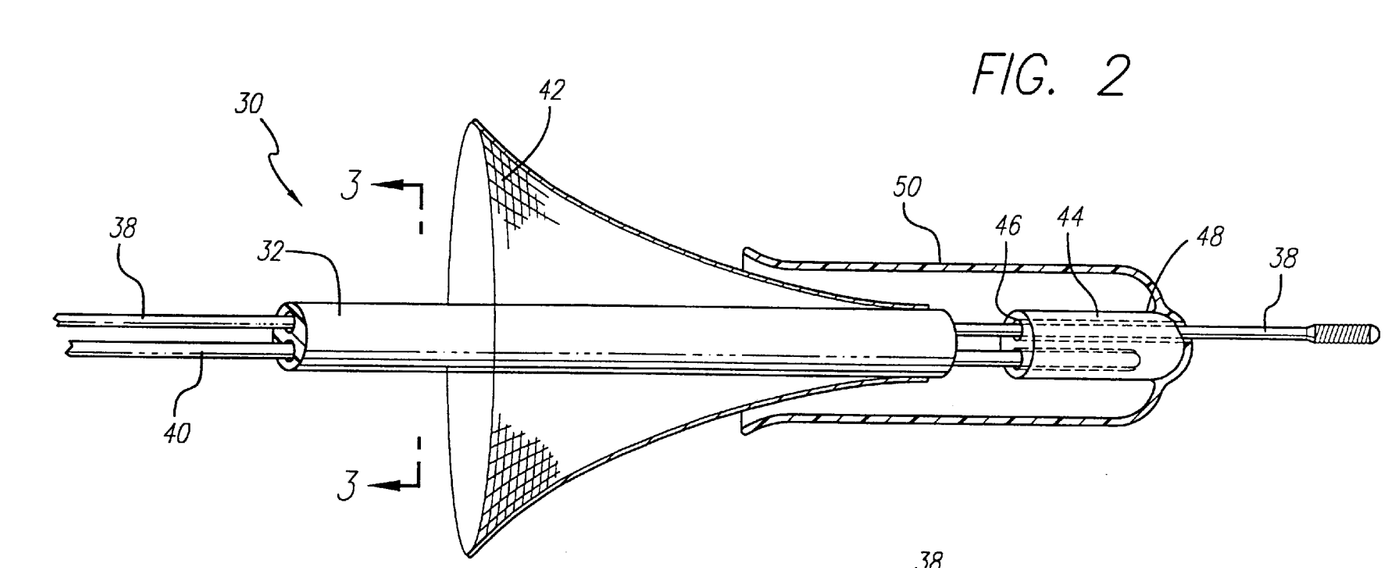
FIG. 2 is a greatly enlarged, partial cross-sectional view of an alternative embodiment of the embolic protection device.
Figure 3:
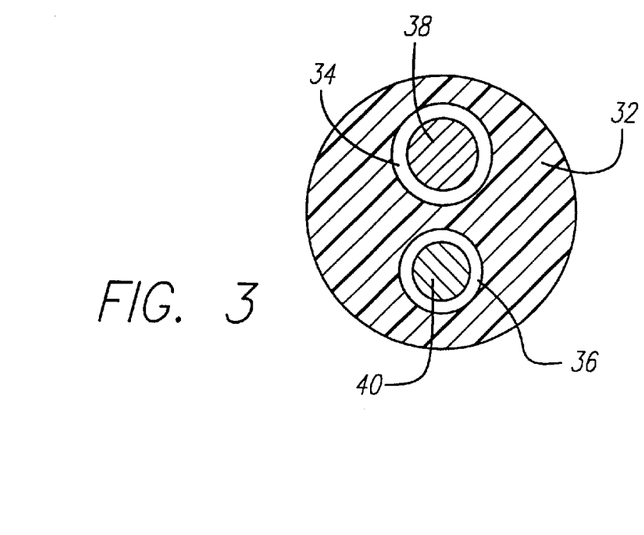
FIG. 3 is an enlarged, axial cross-sectional view of the embodiment of FIG. 2 cut through plane 3—3.

FIGS. 2 and 3 illustrate an alternative embodiment embolic protection device 30 employing a catheter shaft 32 having two lumens 34, 36 formed therein wherein one lumen is dimensioned to accommodate a guidewire 38 and the other lumen is dimensioned to accommodate a push wire 40. Both the catheter and the push wire extend proximally a sufficient distance so as to be manipulatable from outside a patient's vasculature. A conical filtration element 42 is affixed to the distal end of the catheter at its distal end and expands radially outwardly toward its proximal end. Such filtration element has an array of fine perforations formed therein and incorporates a super-elastic material that causes the element to expand when unrestrained. The push wire extends through the lumen formed in the catheter shaft 32 and is positively affixed at its distal end to a tip element 44. Such tip element has lumen 46 formed therein that is axially aligned with the lumen 34 formed in the catheter so as to permit the guidewire 38 to extend there through. The distal end 48 of the tip element has a rounded leading edge and includes sheath 50. The dimensions of such sheath are selected to receive and constrain the filtration element to a reduced diameter. Axially shifting the push wire relative to the catheter causes the sheath to cover and re-cover the filtration element. The filtration element material's memory causes the element to expand when outside the sheath. Forcing the element into the sheath, or alternatively, pulling the sheath over the filtration element causes the element to become reduced in size. The surface of the push wire as well as the surface of the catheter may be coated with a lubricious material in order to reduce friction during the operation of the device.

In use, the guide wire 38 is first maneuvered through the vasculature and through the treatment site to a position downstream therefrom. With the filtration element 42 fully constrained within the sheath 50, the embolic protection device 30 is then advanced over the guide wire to a position downstream of the treatment site and deployed by either holding the catheter shaft 32 in position while proximally advancing the push wire 40 or by holding the push wire in position while retracting the catheter slightly. This frees the filtration element 42 from the sheath 50 and allows it to expand to filter the blood flowing therethrough. After deployment, a primary treatment modality is advanced over the catheter to a position from which the treatment site can be properly accessed. After treatment is completed, the primary modality is removed afterwhich the catheter and push wire are manipulated so as to cause the filtration element to again become constrained within the sheath. Any embolic material that had been captured by the filtration element is thereby tightly retained within the collapsed filtration element as the emboli protection device is removed from the vasculature.

Figures 4, 5:
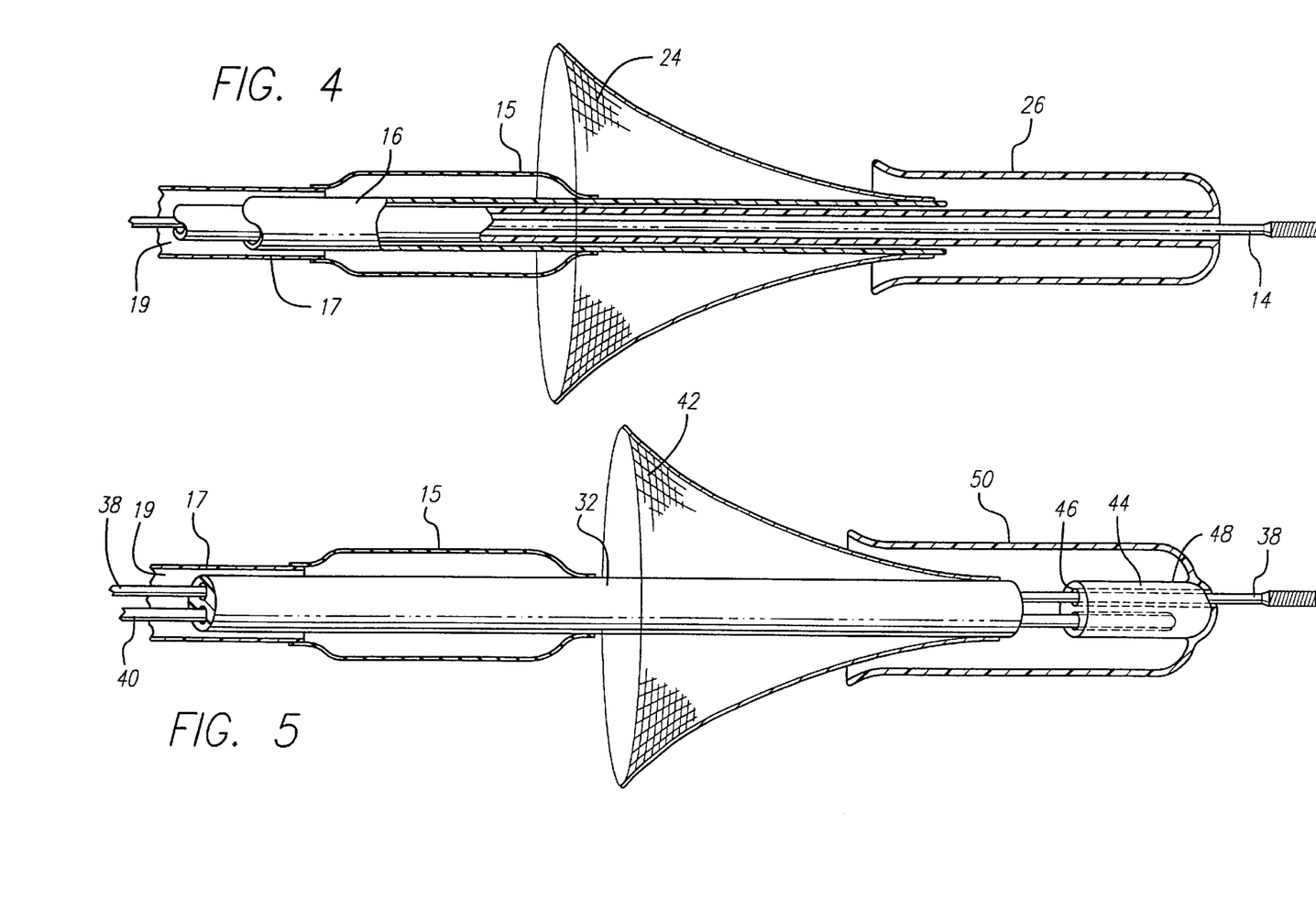
FIG. 4 is an enlarged, partial cross-sectional view of a second alternative embodiment of the embolic protection device with associated treatment modality.
FIG. 5 is an enlarged, partial cross-sectional view of a third alternative embodiment of the embolic protection device with associated treatment modality.

FIG. 4 illustrates an alternative embodiment of the present invention, in which the embolic protection device of FIG. 1 is combined with a treatment modality. In the embodiment shown, a dilatation or stent delivery balloon 15 is attached to the catheter shaft 16, and an outer member 17 is attached to the proximal end of the balloon 15 forming an annular inflation lumen 19 between the catheter shaft 16 and the outer member 17.

FIG. 5 illustrates an alternative embodiment of the present invention, in which the embolic protection device of FIG. 2 is combined with a treatment modality. In the embodiment shown, a dilatation or stent delivery balloon 15 is attached to the catheter shaft 32, and an outer member 17 is attached to the proximal end of the balloon 15 forming an annular inflation lumen 19 between the catheter shaft 32 and the outer member 17.

Figure 6:
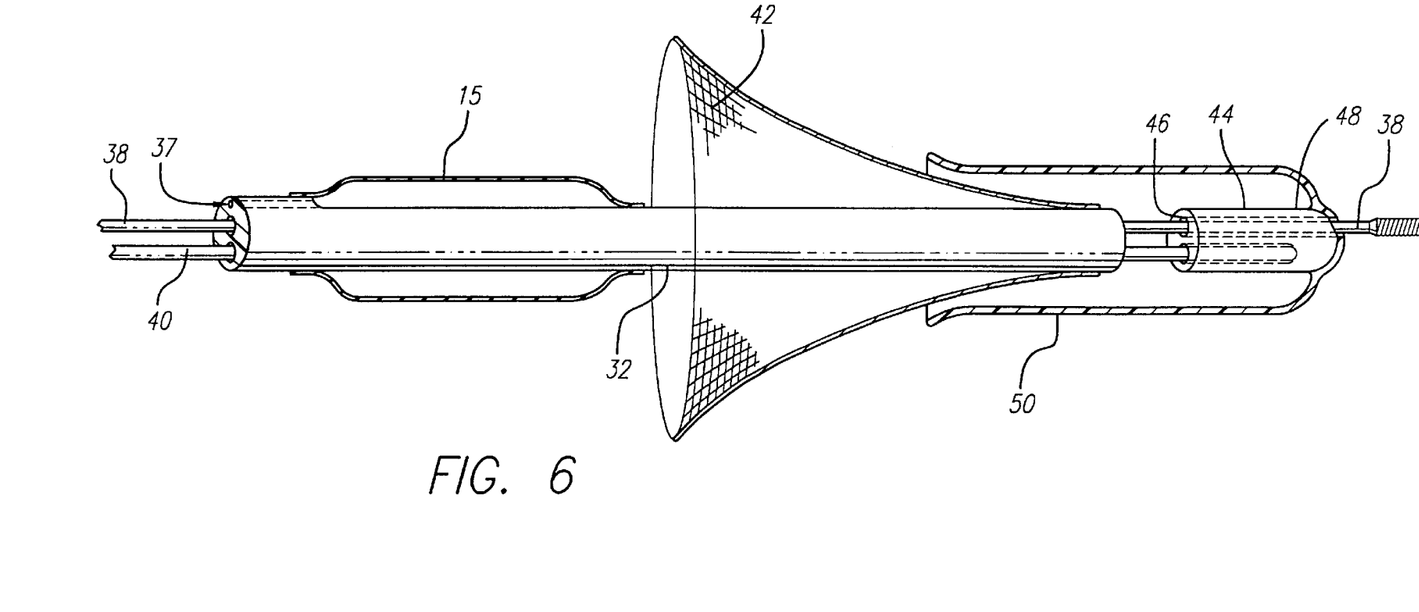
FIG. 6 is an enlarged, partial cross-sectional view of a fourth alternative embodiment of the embolic protection device with associated treatment modality.

FIG. 6 illustrates an alternative embodiment of the present invention, in which the embolic protection device of FIG. 5 has a third lumen 37 in the catheter shaft 32 to provide for inflation and deflation of the balloon.

Figure 7:
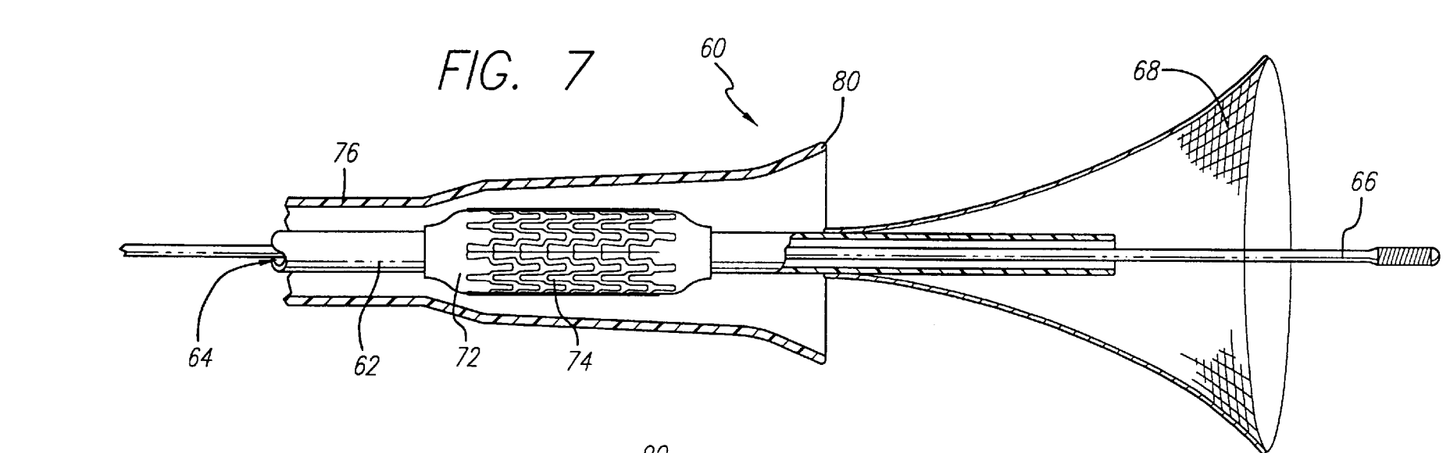
FIG. 7 illustrates an alternative configuration for the outer member.

FIG. 7 illustrates an alternative embodiment 60 wherein the embolic protection device is combined with the treatment modality. A catheter 62 has a lumen 64 formed therein that is dimensioned to accommodate a guide wire 66 therethrough. A conical filtration element 68 is fitted to the distal end of such catheter. The filtration element incorporates a super-elastic material such as Nitinol that causes the element to automatically deploy to its fully expanded configuration when not constrained. Fitted about the catheter at a location proximal to the filtration element is an expandable balloon 72 of a configuration as is well known in the art. A lumen for conducting fluid to and from the balloon to control the degree of inflation of the balloon is not shown. In the embodiment illustrated in FIG. 7, a stent 74 is shown in position about the balloon. An outer sleeve 76 extends along the exterior of the entire assembly. The distal end of such outer member serves as a sheath for constraining the filtration element to a sufficiently reduced diameter to allow it to be maneuvered through a patient's vasculature. The distal end 80 of the outer sleeve may be expanded or flared appropriately to increase the volume to accommodate captured emboli as well as to provide for a smooth mechanical operation during recapture of the filtration element. Similarly, as to all of the embodiments, the distal end of the center sleeve may or may not be flared depending upon the particular application and the size of the conical filtration element. Its proximal end extends a sufficient distance so as to be manipulatable from outside the vasculature. The use of lubricious materials well known in the art may be used to coat the various surfaces that are shifted relative to one another in an effort to reduce friction.

In use, the guide wire 66 is first maneuvered through the vasculature and through the treatment site to a position downstream of the treatment site. With the filtration element 68 fully constrained within the outer sleeve 76, the embolic protection device 60 is then advanced along the guide wire to a position wherein the balloon 72 and stent 74 are aligned with the treatment site. While the catheter 62 is held in position, the outer sleeve 76 is retracted slightly to release the filtration element 68 which self-expands to assume its deployed configuration. Further retraction of the outer member exposes the stent which may then be deployed by inflation of the underlying balloon 72. Once the stent is fully deployed and the balloon has been deflated, the outer sleeve 76 is advanced over the balloon and through the expanded stent. As the outer member is advanced further, the entire filtration element, along with any entrapped embolic debris becomes constrained within the outer sleeve thereby allowing the entire embolic protection device to be removed from the patient's vasculature.

Figure 8:
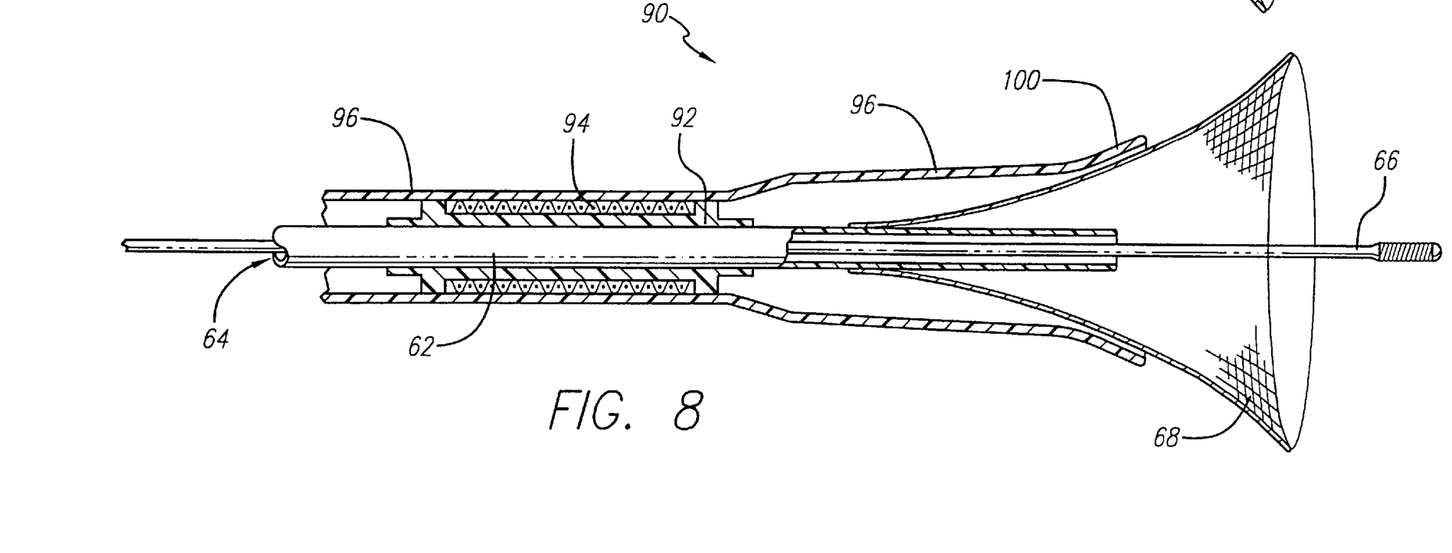
FIG. 8 illustrates another alternative configuration for the outer member with a different incorporated treatment modality.

FIG. 8 is a variation of the device shown in FIG. 7 wherein an alternative primary treatment modality is employed, namely, a self-expanding stent sans expandable balloon. Fitted about the catheter 62 at a location proximal to the filtration element 68 is a stent saddle 92 about which a self-expanding stent 94 is fitted. Such stent configurations are well known and rely on super-elastic material to cause the stent to expand when unrestrained. The outer sleeve 96 not only serves to control the deployment and the recapture of the filtration element but also serves to constrain the stent. The use of lubricious materials well known in the art to coat the various surfaces that are shifted relative to one another greatly reduces friction.

In use, the guide wire 66 is first introduced into the vasculature and advanced past the intended treatment site. With the filtration element 68 fully constrained within the outer sleeve 96, the embolic protection device 90 is advanced over the guide wire to a position wherein the stent 94 is aligned with the treatment site. While maintaining the catheter 62 in position, the outer sleeve 96 is retracted to release the filtration element 68 which self-expands to its fully deployed configuration. Further retraction of the outer sleeve releases the stent which self-expands to engage and support the body lumen walls. The outer sleeve is subsequently advanced over the catheter and through the deployed stent to engage and gradually collapse the filtration element. As the outer sleeve is advanced further, it fully encapsulates the filtration element and any embolic debris that had been captured therein. Once fully constrained to the reduced diameter, the entire embolic protection device is removed from within the vasculature.

Figure 9:
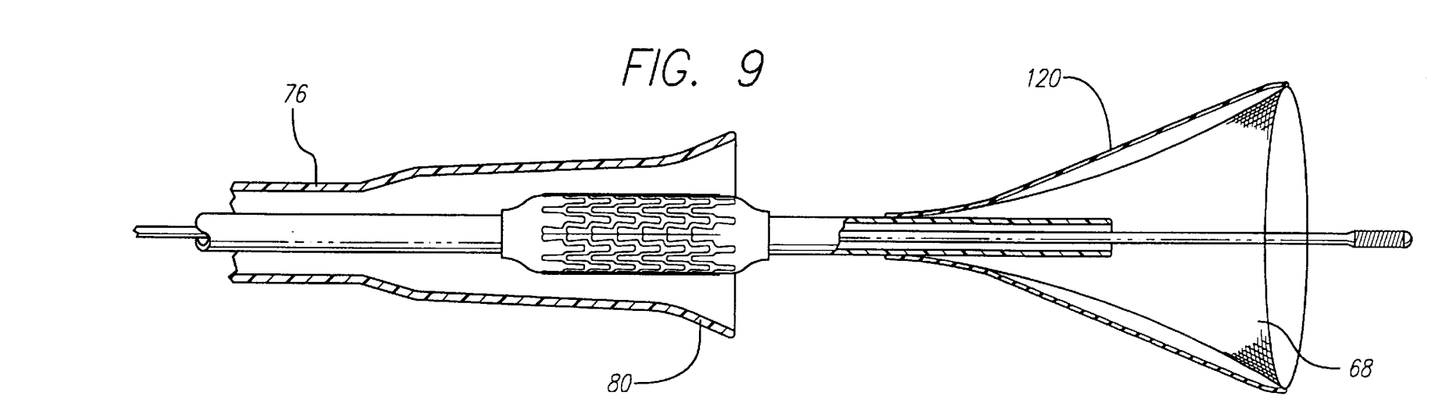
FIG. 9 illustrates an alternative embodiment with the addition of guiding ribs.

FIG. 9 illustrates an alternative embodiment of the present invention, in which the embolic protection device of FIG. 7 includes a series of raised guiding ribs 120 disposed on the exterior surface of the filtration element 68. The guiding ribs 120 assist in the deployment and recovery of the filtration element 68, and may serve to alter the shape of the filtration element 68 to better allow it to collect and retain embolic debris. The may or may not be firmly attached to the filtration element 68 at any point, and may or may not be made of super-elastic material like the filtration element.

Figure 10:
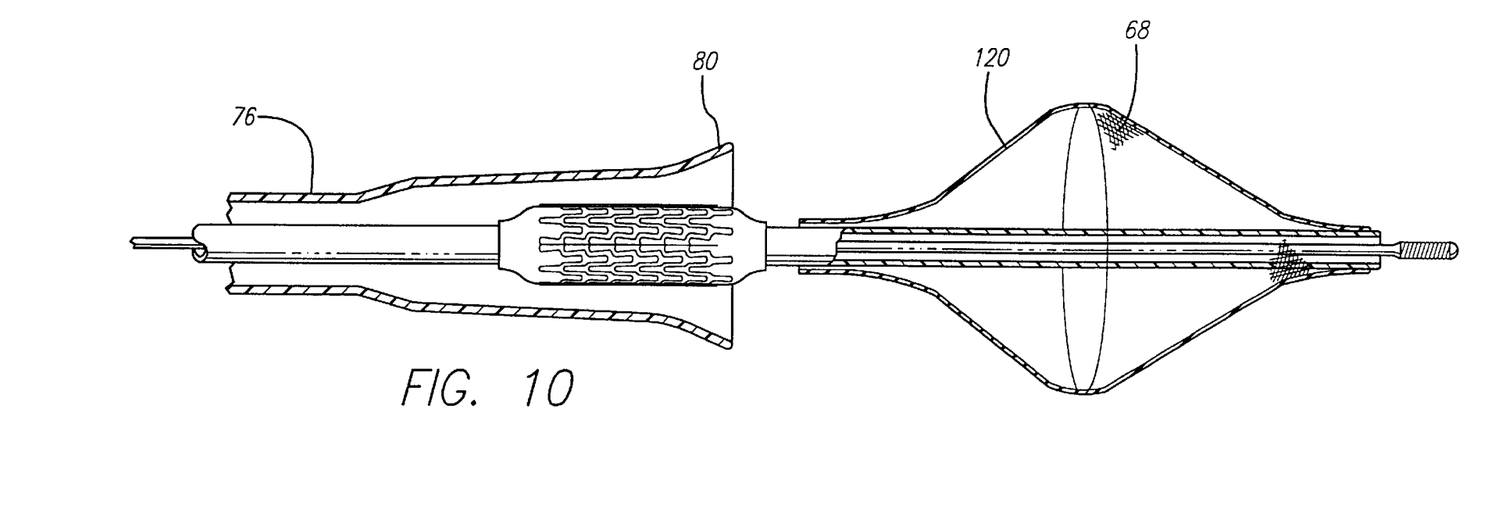
FIG. 10 illustrates an alternative configuration for the guiding ribs.

FIG. 10 illustrates an alternative embodiment of the present invention, in which the embolic protection device of FIG. 9 has the filtration element 68 mounted such that the expanded end lies proximal. The guiding ribs 120 likewise assist in the deployment and recovery of the filtration element 68, and may serve to alter the shape of the filtration element 68 to better allow it to collect and retain embolic debris. They may or may not be firmly attached to the filtration element 68 at any point, and may or may not be made of a super-elastic material like the filtration element. During recovery of the filtration element, the guiding ribs 120 may act as tendons to assist in the collapsing of the filtration element during advancement of the outer sleeve. The use of guiding ribs can be employed in any of the other heretofore described embodiments of the present invention.

The filtration element employed in the various embodiments of the present invention is formed of a super-elastic material that causes the element to self-expand when not constrained. Super-elastic material such as Nitinol may be employed wherein the filtration element is first formed and then its shape is set using standard process techniques as are well known in the art of forming stents. As an example, both the filtration element as well as the guiding ribs shown in FIGS. 9 and 10 could be laser machined from super-elastic Nitinol tubing as an integrated component obviating the effort and complications inherent in attempting to weld or otherwise attach the guiding ribs to the filtration element. Because radial strength is not a critical design parameter for the filtration element, an extremely flexible combination of material and/or structural configuration may be employed to provide for a low-profile, easy to deploy and retrieve embolic protection device. As an alternative to the use of Nitinol, laser perforated or bored polyurethane, nylon or other appropriate polymer may be employed to fabricate the filtration element. Further options include the use of braided polymers such as Dacron or the use of braided wire. The filtration element is subsequently joined to the catheter using traditional joining techniques.

FIGS. 7–10 illustrate embodiments wherein the sheath portion of the outer sleeve 76, 96 that receives the filtration element is configured in the form of constant diameter. Alternatively, the sheath portion may be configured in the form of an open flare having a diameter that gradually increases toward the leading edge 80 and 100. The flare may be dimensioned so as to extend along the entire length of the filtration element or may be significantly shorter so as to merely present a raised leading edge to facilitate the entry of the filtration element thereinto. The outer sleeve may formed of a semi-compliant material that is elastic such as for example low durometer Pebax. The material gives slightly as the filtration element is received within the sheath so as to accommodate the filtration element and any embolic material contained therein. A further alternative embodiment exists wherein the outer member is fabricated of multi-layer tubing. The inner layer may consist of a low durometer Teflon, HDPE or similar material that promotes smooth retraction of a filter element thereinto. The middle layer may consist of a stainless steel braid so as to provide both radial as well as axial support to the sheath and outer member. The outer layer may consist of a low durometer material such as Pebax to encapsulate the braid and provide structural integrity to the outer member. Additionally, a low friction outer surface promotes atraumatic delivery and retraction of the device. The braided layer may run the entire length of the outer member, may be limited to the distal section approximately corresponding to the sheath element or may be deleted altogether. The thickness of the various sections may be selected to optimize the support requirements of a particular application. The sheath element of the outer member may comprise an expanded section of constant diameter.

While a particular form of the invention has been illustrated and described, it will also be apparent to those skilled in the art that various modifications can be made without departing from the spirit and scope of the invention. For example, in addition to using the embolic protection device of the present invention as a stand-alone tool for retrieving clots or in combination with a stent and associated delivery apparatus, the device can be used in conjunction with other primary treatment modalities which would include but would not be limited to stand-alone angioplasty devices, photo-acoustic clot destroying devices and drug delivery devices. Accordingly, it is not intended that the invention be limited except by the appended claims.

What is claimed:

1. An over-the-wire embolic protection device, comprising:
   a catheter having a first lumen formed therein;
   a self-expanding filtration element affixed about the distal end of said catheter, formed so as to assume a generally conical shape of preselected maximum diameter when not constrained;
   a sheath, substantially axially aligned with said catheter, longitudinally shiftable relative to said filtration element and dimensioned to constrain said filtration element to a reduced diameter; and
   an inner member disposed within said first lumen of said catheter so as to be longitudinally shiftable therein, said inner member having a lumen formed therein dimensioned to accommodate a guidewire and wherein said inner member is attached to said sheath at its distal end while its proximal end extends towards the proximal end of the device.

2. The embolic protection device of claim 1, wherein said filtration element is formed of a polymeric material.

3. The embolic protection device of claim 1, wherein said filtration element is formed of a super-elastic material.

4. An over-the-wire embolic protection device, comprising:
   a catheter having a first lumen formed therein;
   a self-expanding filtration element affixed about the distal end of said catheter, formed so as to assume a generally conical shape of preselected maximum diameter when not constrained;
   a sheath, substantially axially aligned with said catheter, longitudinally shiftable relative to said filtration element and dimensioned to constrain said filtration element to a reduced diameter; and
   means for shifting said sheath relative to said filtration element from the proximal end of the device, wherein said catheter is dimensioned to slidably receive a primary treatment modality thereover.

5. An over-the-wire embolic protection device, comprising:
   a catheter having a first lumen formed therein;
   a self-expanding filtration element affixed about the distal end of said catheter, formed so as to assume a generally conical shape of preselected maximum diameter when not constrained;
   a sheath, substantially axially aligned with said catheter, longitudinally shiftable relative to said filtration element and dimensioned to constrain said filtration element to a reduced diameter; and
   means for shifting said sheath relative to said filtration element from the proximal end of the device, wherein said catheter has a primary treatment modality fitted thereto at a location proximal to said filtration element.

6. The embolic protection device of claim 5, wherein said primary treatment modality comprises an expandable balloon.

7. The embolic protection device of claim 5, wherein said primary treatment modality comprises a stent and stent delivery mechanism.

8. The embolic protection device of claim 7, wherein said stent delivery mechanism comprises an expandable balloon.

9. The embolic protection device of claim 7, wherein said delivery mechanism relies on a self-expanding stent.

10. The embolic protection device of claim 9, wherein said shifting means comprises an outer member that is disposed about said catheter, is longitudinally shiftable thereon and extends towards its proximal end, wherein such outer member serves to constrain said self-expanding stent and where the distal end of said outer member defines said sheath.

11. The embolic protection device of claim 5, wherein said primary treatment modality comprises an expandable member.

12. An over-the-wire embolic protection device, comprising:
    a catheter having a first lumen formed therein dimensioned to accommodate a guide wire and a second lumen formed therein;
    a self-expanding filtration element affixed about the distal end of said catheter, formed so as to assume a generally conical shape of preselected maximum diameter when not constrained;
    a sheath, substantially axially aligned with said catheter, longitudinally shiftable relative to said filtration element and dimensioned to constrain said filtration element to a reduced diameter; and
    a pushwire attached to said sheath at its distal end which extends proximally therefrom within said second lumen for shifting said sheath relative to said filtration element from the proximal end of the device.

13. The embolic protection device of claim 12, wherein said pushwire is attached to said sheath by a tip element having a lumen formed therein that is longitudinally aligned with said first lumen of said catheter and dimensioned to accommodate a guidewire.

14. An over-the-wire embolic protection device, comprising:
    a catheter having a first lumen formed therein;
    a self-expanding filtration element affixed about the distal end of said catheter, formed so as to assume a generally conical shape of preselected maximum diameter when not constrained;
    a sheath, substantially axially aligned with said catheter, longitudinally shiftable relative to said filtration element and dimensioned to constrain said filtration element to a reduced diameter; and
    an outer member that is disposed about said catheter and extends towards its proximal end; wherein the distal end of said outer member defines said sheath and said filtration element is oriented such that it is attached to said catheter at its distal end and is expanded radially outwardly at its proximal end.

15. The embolic protection device of claim 14, wherein a plurality of guiding ribs are attached to the proximal end of said filtration element that extend proximally along said catheter.

16. An over-the-wire embolic protection device, comprising:
    a catheter having a first lumen formed therein;
    a self-expanding filtration element affixed about the distal end of said catheter, formed so as to assume a generally conical shape of preselected maximum diameter when not constrained;
    a sheath, substantially axially aligned with said catheter, longitudinally shiftable relative to said filtration element and dimensioned to constrain said filtration element to a reduced diameter;
    a plurality of longitudinally raised guiding ribs are fitted to the exterior surface of said filtration element; and
    an outer member that is disposed about said catheter and extends towards its proximal end, wherein the distal end of said outer member defines said sheath and said filtration element is oriented such that it is attached to said catheter at its proximal end and is expanded radially outwardly at its distal end and said catheter is dimensioned to slidably receive a primary treatment modality thereover.

* * * * *